(12) United States Patent
Shepherd

(10) Patent No.: US 8,372,631 B2
(45) Date of Patent: Feb. 12, 2013

(54) SYSTEM FOR HARVESTING ALGAE IN CONTINUOUS FERMENTATION

(75) Inventor: Samuel L. Shepherd, Houston, TX (US)

(73) Assignee: Missing Link Technology, LLC, Houston, TX (US)

( * ) Notice: Subject to any disclaimer, the term of this patent is extended or adjusted under 35 U.S.C. 154(b) by 590 days.

(21) Appl. No.: 12/631,147

(22) Filed: Dec. 4, 2009

(65) Prior Publication Data

US 2010/0144017 A1    Jun. 10, 2010

Related U.S. Application Data

(60) Provisional application No. 61/120,550, filed on Dec. 8, 2008.

(51) Int. Cl.
*C12M 1/00* (2006.01)
(52) U.S. Cl. .................................. 435/290.4; 435/257.1
(58) Field of Classification Search ............... 435/290.4, 435/257.1
See application file for complete search history.

(56) References Cited

U.S. PATENT DOCUMENTS

2010/0050502 A1 * 3/2010 Wu et al. ..................... 44/308

* cited by examiner

*Primary Examiner* — Michael Marcheschi
*Assistant Examiner* — Jonathan Hurst
(74) *Attorney, Agent, or Firm* — Egbert Law Offices, PLLC

(57) ABSTRACT

The present invention is a system for harvesting algae in continuous fermentation. There is a harvester including a main moving belt, a plurality of rollers, and a motor for driving the main moving belt. There is a reactor tank and a vacuum extractor for applying a vacuum over a width of the main moving belt to extract biomass and to dry the main moving belt. The main moving belt has one end in the reactor tanks and another end extended into the vacuum extractor. The algae contained in the reactor tank is collected for further processing, including oil extraction. With algae harvested in the large-scale manner of the present invention, a more efficient oil extraction method can be used because the concentration, temperature, and pressure can be more easily controlled.

9 Claims, 2 Drawing Sheets

SYSTEM FOR HARVESTING ALGAE IN CONTINUOUS FERMENTATION

RELATED U.S. APPLICATIONS

The present application claims priority from U.S. Provisional Patent Application Ser. No. 61/120,550, filed on Dec. 8, 2008 and entitled "SYSTEM FOR HARVESTING ALGAE IN CONTINUOUS FERMENTATION."

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to systems for harvesting biological material. More particularly, the present invention relates to a system for harvesting algae for use in continuous fermentation. Additionally, the present invention also relates to a system for fermentation using algae as the microorganism.

2. Description of Related Art Including Information Disclosed Under 37 CFR 1.97 and 37 CFR 1.98

Research into efficient algal-oil production is currently being done in the private sector. Using algae to produce biodiesel may be a viable method by which to produce enough fuel to eliminate the dependence upon harvesting fossil fuels from non-sustainable resources. Algae require sunlight, carbon dioxide, small amounts of micronutrients, water, and small amounts of heat to grow. Given the proper conditions, some algae can double its mass in less than twelve (12) hours. Importantly, algae can produce a portion their biomass in the form of oil. Because the algae grows in an aqueous suspension, they are capable of producing large amounts of biomass and usable oil in either high rate algal ponds or photobioreactors. This oil can then be processed into usable fuel.

The algal industry is comprised of three major phases: growth, harvest, and utilization. Each phase requires different technologies to achieve economic viability. Each phase must become more efficient in order to support development and use of this sustainable resource. The difficulties in efficient and commercially viable biodiesel production from algae lie in establishing a reliable and resilient algal strain with a high lipid content and fast growth rate with a cost-effective cultivation system, such as a photobioreactor, that is optimized for that particular strain. This algal must also be amenable to harvesting without too much difficulty.

The growth phase is accomplished using technologies and media that are conducive to a specific algae species. Research has focused on algae growth for several years. Maximizing algae growth is one way of progressing towards commercially viable algal-oil production. The mass-production of oil by algae is mainly focused on microalgae; these organisms are capable of photosynthesis at less than 0.4 mm in diameter, including the diatoms and cyanobacteria. The macroalgae, like seaweed, have high availability, but the microalgae is less complex, grows faster, and contains a higher oil content in certain species.

Similarly, the utilization phase is accomplished using known and developing technologies for the processing of algal biomass and oils into usable fuel and materials. The applications are already known for using the algal-oil products. The demand for the biomass and oils currently surpasses the current industry's ability to supply.

The harvest phase is a key area of the algal-oil production field, requiring improvement before truly commercially viable production can be sustained. There are two major concerns for overcoming the lack of ability and technology to economically harvest the extract the oil and chemicals from the algae. First, since algae grows in an aqueous environment to optimal concentration levels of between 300 and 1500 ppm, large volumes of water must be pumped or transferred in order to harvest small amounts of dry algae. This hefty water requirement restricts the ability to scale up algal bioreactors to commercial levels. Second, extracting the oil and chemicals from the harvested algae currently requires uneconomical extraction methods, such as super critical $CO_2$, ultrasonics, and solvent extraction. These restrictive limitations have so far inhibited true commercialization of algae to energy.

With regard to the large water requirement, open-pond systems were the first attempt at high volume cultivation of algae with high-oil content. These open system were flawed because of dependence upon resiliency of a particular algae strain in terms of temperature and pH and upon hardiness to compete against invading algae and bacteria. These single species systems were also vulnerable to viral infection. The open-pond systems required algal species with lower oil content because the algae had to divert energy and resources to proteins and carbohydrates to survive the environmental conditions. The high-oil content algal strain invests more resources into the production of oil, but they could not survive the conditions and had a slower growth rate.

The later focus on closed systems, not being exposed to open air, encountered a different problem. The closed system must located a cheap source of sterile carbon dioxide ($CO_2$), and there have not been many cost-effective options. Although the possibility of placement near power plants to soak of pollution has been disclosed in the prior art.

With regard to the extraction methods, it has become a priority of large scale algal-cultivation system to looking for incorporating into existing infrastructures, such as coal power plants or sewage treatment facilities. This approach not only provides the raw materials for the system, such as $CO_2$ and nutrients, but the connection converts those wastes into resources.

In the past, various patents have been issued in the field of fermentation, relating to processing bio-harvests. For example, U.S. Pat. No. 6,599,735, issued on Jul. 29, 2003 to the Bartok et al., describes fermentation assembly comprising a vessel for culturing living cells, at least two storage flasks in fluid communication with the vessel for supply of liquids and a first transport means for transferring the liquids from the storage flasks to the vessel, individual appliances operably connected to the transport means for monitoring the supply of the contents of the storage flasks to the vessel, a harvest flask in fluid communication with the vessel and a second transport means for transferring the fermentation broth from the vessel to the harvest flask, and a device operably connected to the first transport means for controlling and maintaining a constant dilution rate in the vessel with varying rates of individual supply of liquid from the storage flasks to the vessel.

U.S. Pat. No. 5,688,674, issued on Nov. 18, 1997 to Choi et al., describes a metabolite, e.g., ethanol, that is continuously produced from low cost carbohydrate substrates by a process which comprises pulverizing the carbohydrate substrate, liquefying and saccharifying the pulverized substrate, continuously fermenting the lique-saccharified substrate in a fermentor equipped with a moving filter, in the presence of flocculent biological cells maintained at a concentration ranging from 90 to 160 g/l by using the moving filter and a culture medium to produce a fermentation product mixture, and recovering the desired metabolite from the fermentation product mixture.

U.S. Pat. No. 4,069,149, issued on Jan. 17, 1978 to Jackson, describes a deep-tank reactor utilized for fermentation of waste liquid or other liquid in a biological reaction resulting in a solid cellular material. The resulting solid material, which is in suspension, is initially separated from the bulk of the liquid by a gaseous flotation process, using the dissolved gas in the liquid as the source of gaseous bubbles for flotation purposes.

U.S. Pat. No. 4,286,066, issued on Aug. 25, 1981 to Butler et al., describes an apparatus for continuously fermenting a moist particulate feed and distilling the fermentation product where a pressure-locked auger forces a moist particulate feed from a hopper into a fermentation tank. Liquor is removed from the tank, and solids are separated therefrom to produce a beer which is distilled in a distillation column. A combustion engine powers the auger and the means for separating solids, and the engine exhaust surrounds an inlet section of said auger to help heat the pressurized feed therein to produce fermentable sugar within the auger, and the auger includes a section passing to the tank in heat exchange relation to the distillation column to provide heat for distillation. The column is a multistage column angled to face the sun and has an upper glass plate to allow solar radiation to enter and penetrate between the foraminous plates of the column.

It is an object of the present invention to provide a system for continuous fermentation using algae.

It is another object of the present invention to eliminate the large volumes of water required for harvesting algae.

It is another object of the present invention to extract oil from harvested algae using an economical method.

It is yet another object of the present invention to provide an optimal reactor structure for any given set of operating conditions.

It is still another object of the present invention to provide concentrated algae for more efficient collection.

These and other objects and advantages of the present invention will become apparent from a reading of the attached specification.

SUMMARY OF THE INVENTION

The present invention is a system for harvesting algae in continuous fermentation. There is a harvesting means comprised of a main moving belt, a plurality of rollers, and a motor means for driving the main moving belt. There is a reactor tank, wherein the main moving belt has one end within an interior of the reactor tank and at least one roller placed along a predetermined length of the reactor tank. The main moving belt passes through the reactor tank filled with the fermenting algae. Each pass through the reactor tank forces algae onto the main moving belt for transport to another end of the main moving belt.

The present invention also includes a vacuum extraction means for applying a vacuum over a width of the main moving belt to extract biomass and to dry the main moving belt. The main moving belt has its other end extended into the vacuum extraction means. The algae, from the reactor tank is brought to the vacuum extraction means by the main moving belt for collection and concentration of the algae. A stabilizer is part of the vacuum process because the stabilizer includes at least two belts placed around the main moving belts. A collection means for holding extracted biomass is located at another end of the vacuuming process so that the harvested and concentrated algae can be moved to the next stage in processing to extract the oil.

There can also be post-extraction means for air drying or washing or both. For example, another vacuum can be applied over a width of the main moving belt after the main moving belt passes through the vacuum extraction means and the collection means. The post-extraction means cleans the main moving belt before returning to the reactor tank so that more algae can be delivered to the vacuum extraction means.

After the algae has been collected, this harvested algae can be processed to extract the oil. With harvested algae, a more efficient extraction method can be used because the concentration, temperature, and pressure can be more easily controlled. In particular, gas is injected into a biomass stream containing a liquid portion and a solid portion, the harvested algae. Gas is dissolved into the liquid portion under controlled temperature and pressure so that gas defuses into the cellular structure of the algae for a predetermined amount of time. The biomass stream is flashed in less than 0.5 seconds to burst the cell structure of the algae. The oil is collected using known methods, such as gravity separation, mechanical separation, centrifugation, and others.

DETAILED DESCRIPTION OF THE DRAWINGS

Figure 1:
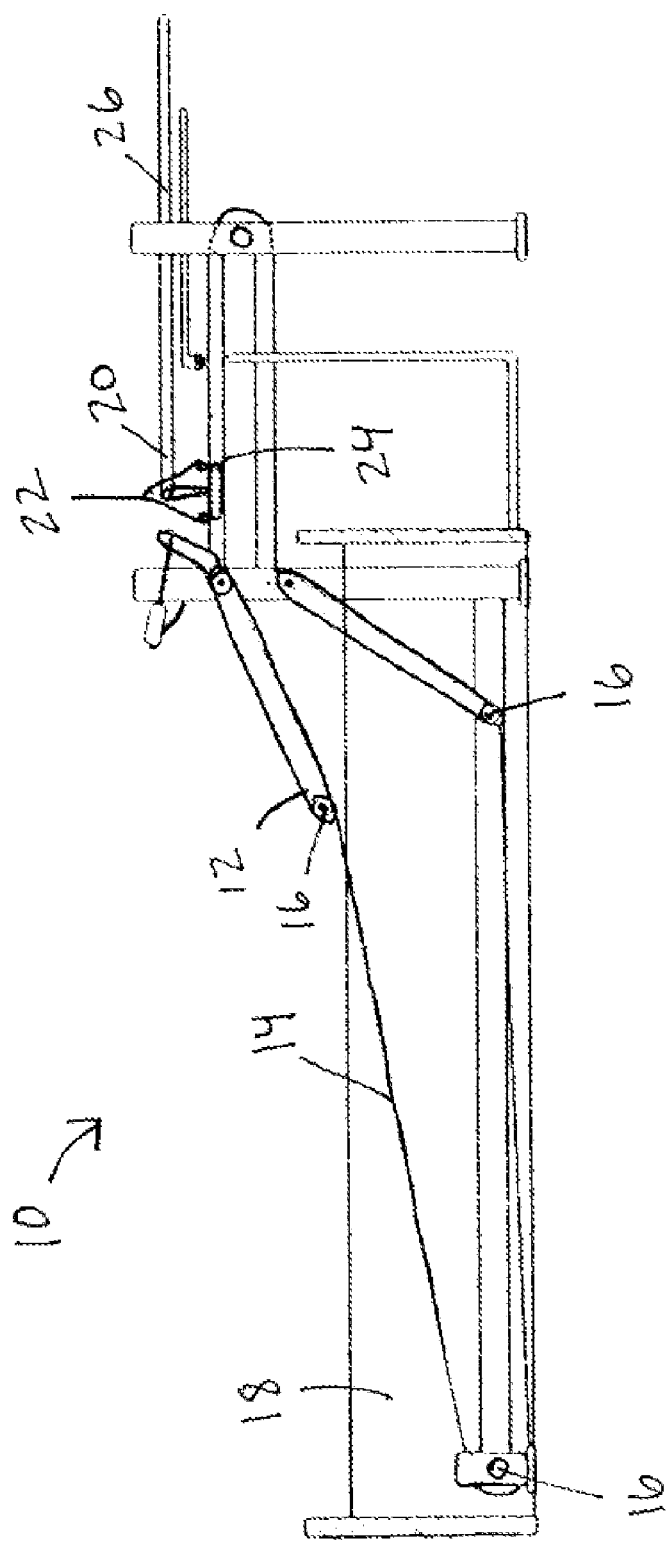
FIG. 1 is a cross-sectional view of the system for harvesting algae of the present invention.
Figure 2:
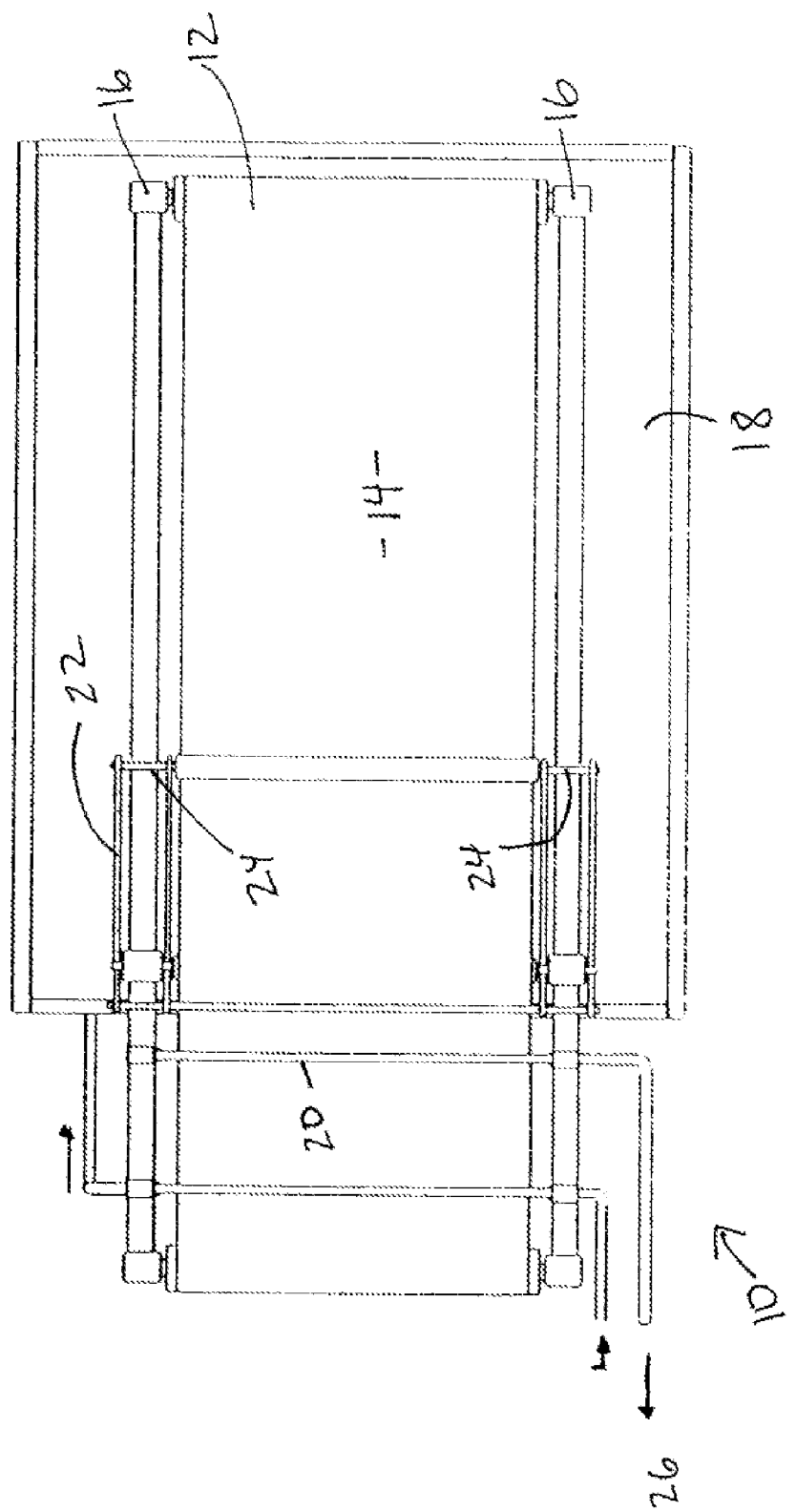
FIG. 2 is a top plan view of a schematic illustration of the harvesting system utilizing the fermentation reactor of the present invention.

Referring to FIG. 1, the system 10 for harvesting algae in continuous fermentation of the present invention is shown. The system 10 includes a harvesting means 12 being comprised of a main moving belt 14, a plurality of rollers 16, and a motor means (not shown) for driving the main moving belt 14. The system 10 also includes a reactor tank 18, which stores the fermenting algae. The main moving belt 14 has one end within an interior of the reactor tank 18 and at least one roller 16 placed along a predetermined length of the reactor tank 18. The main moving belt 14 passes through the reactor tank 18 filled with the fermenting algae. Each pass through the reactor tank 18 forces algae onto the main moving belt 14 for transport to another end of the main moving belt 14. The algae is moved without the need for large amounts of water.

The present invention also includes a vacuum extraction means 20 for applying a vacuum over a width of the main moving belt 14 to extract biomass and to dry the main moving belt 14. The main moving belt 14 has its other end extended into the vacuum extraction means 20. The algae contained in the reactor tank is brought to the vacuum extraction means 20 by the main moving belt 14 for collection and concentration of the algae. A stabilizing means 22 is included to hold the main moving belt 14 in place when subjected to the vacuum. The main moving belt 14 is placed between the at least two belts in the vacuum extraction means 20. The stabilizing means 22 is comprised of at least two belts 24. There is also a collection means 26 for holding extracted biomass, namely algae. The collection means 26 is located at another end of the vacuum extraction means 20 so that the harvested and concentrated algae can be moved to the next stage in processing to extract the oil.

In FIG. 1, at least one roller 16 is positioned at a bottom of the reactor tank 18 so as to submerge a portion of the main moving belt 14 for maximum exposure to algae in the reactor tank 18. Alternatively, there can be at least two rollers 16 positioned on a bottom of the reactor tank 18 at opposite ends of the reactor tank so as to expose the main moving belt to algae lengthwise along the reactor tank 18. Furthermore, the main moving belt 14 has at least one end extending out of the reactor tank 18 with an inclined surface from one end within the interior of the reactor tank 18 upward to another end extending out of the reactor tank 18. As such, the vacuum extraction means 20 is positioned higher than the reactor tank 18, and the collection means 26 is at an opposite end of the main moving belt 14 from the reactor tank 18.

There can also be post-extraction means for air drying or washing or both. For example, another vacuum can be applied over a width of the main moving belt after the main moving belt passes through the vacuum extraction means and the collection means. The post-extraction means cleans the main moving belt before returning to the reactor tank so that more algae can be delivered to the vacuum extraction means. In particular, the post-extraction means is placed along the main moving belt 14 after the main moving belt 14 passes through the vacuum extraction means 20 and the collection means 26 and before returning to the reactor tank 18.

The method for harvesting algae in continuous fermentation includes moving a main moving belt through a reactor tank, transporting algae on the belt to a vacuum extractor to remove algae from the belt, stabilizing the belt during exposure to the vacuum extractor, collecting algae from the vacuum extractor as biomass for oil harvesting, returning the belt to the reactor tank; and repeating movement of the belt for continuous harvest of algae. The step of transporting comprises moving the belt at an upward incline to the vacuum extractor positioned higher than the reactor tank. The step of moving the belt can comprise placing at least two rollers on a bottom of the reactor tank for submerging a portion of the belt lengthwise along the bottom of the reactor tank.

The reactor tank contains algae, and the belt moves by rollers with a submerged portion in the reactor tank. The reactor tank contains algae set by general formula:

$$\text{Rate of algal growth} = d[\text{Calgae}]/dt = k2[\text{Calgae}](2-n) \times k1e(-2 \times \text{time}/24)$$

wherein $K1 = b \times \exp(A \times \text{temp } C)$, $k2 = [\text{Calgae}] \times nk3$, $n = 0.08/(\text{light energy} \times \%\text{ light absorption efficiency})$, $2 \times \text{time} = $ rate for biomass double at temp C in hours, $[\text{Calgae}] = $ algal concentration ppm (v/v), $k3 = 2.8$, $A = 0.3535$, and $b = 0.0346$.

The system for harvesting algae of the present invention may also include a processor for the collected algae in the collection means 26. This processor may include an oil extractor, a gasifier, a pre-heater, an injector, a separator for isolating solid, liquid, and gas phase contents, and a collector for the oil of the contents. The processor applies an extracting method to the collected algae from the reactor tank 18. The end result is a source of oil from the biomass of the algae, which can be used in further oil applications.

The method for harvesting algae may also include extracting oil from the biomass using the processor after the collection means 26. The extraction is accomplished by pumping collected biomass under pressures between 500 and 2000 psig at temperatures from ambient to 1400 deg F.; releasing pressure in less than 0.5 secs, causing algal cell structures to burst; and collecting oil from burst cell contents. Known methods of collecting oil are applied, such as gravity separation, mechanical separation, centrifugation, and flocculation. De-emulsifiers may also be added to enhance and improve separation of oil from burst cell content.

After the algae has been collected at collection means 26, the harvested algae can be processed to extract the oil. A more efficient extraction method can be used because the concentration, temperature, and pressure can be more easily controlled. For example, the Alginator™ process can be used to extract the oil. This particular process comprising: pumping the collected biomass under pressures between 500 and 2000 psig at temperatures from ambient to 1400° F.; releasing the pressure in less than 0.5 s, thereby causing the algal cell structures to burst. This action releases the oil from the cellular structure. The oil is collected through standard acceptable methods including, but not limited to, gravity separation, mechanical separation, centrifugation, flocculation etc and may incorporate the use of demulsifiers to enhance and improve the separation times.

The injection of gas into the biomass stream containing the harvested algae can be controlled to dissolve under controlled temperature and pressure, so that gas defuses into the cellular structure of the algae for a predetermined amount of time. The biomass stream is flashed to burst the cell structure of the algae. The optimal reactor structure can be adjusted for a given set of operating conditions so that the most efficient and economical extraction can be used for a particular biomass stream of the harvested algae. The harvesting action provides a concentrated biomass stream for more efficient collection of the desired biofuel.

With regard to the harvester of the present invention, the main moving belt 14 eliminates the need for large amounts of water for transporting large amounts of algae. The main moving belt 14 is driven continuously along the submerged portion of the reactor tank 18 to the vacuum extraction means 20, so that the harvesting cycle is repeated, resulting in continuous harvesting of concentrated algae from the reactor at 1/60th the cost of pumping the water/algae. The harvested algae and water can be further dried, or processed into biomass, biocrude or oil/chemical extraction. The process comparison and Horsepower requirements of using the present invention and using the prior art water pumping are found in TABLE I. As such, the present invention represents significant cost and resource savings for the commercialization of the biofuel.

The foregoing disclosure and description of the invention is illustrative and explanatory thereof. Various changes in the details of the illustrated construction and method can be made without departing from the true spirit of the invention. The present invention should only be limited by the following claims and their legal equivalencies.

TABLE I

OPERATING COMPARISION

| | | units | value |
|---|---|---|---|
| Algae concentration minimum | | ppm | 300 |
| Algae concentration @ harvest | | ppm | 2,400 |
| Unit Reactor | length | ft | 100,000 |
| | width | ft | 24 |
| | depth | ft | 2 |
| | Volume | cuft | 4,800,000 |
| | | gallons | 35,904,000 |
| | | lbs | 299,439,360 |

TABLE I-continued

OPERATING COMPARISION

| | units | value |
|---|---|---|
| Growth rate | cycles/day | 3 |
| Recirculation Rate | ft/min | 3 |
| Dry mass algae | lbs/day | 628,823 |
| | tons/day | 314 |
| | tons/yr | 114760 |
| | oil content | 0.3 |
| | gals oil/yr | 8,256,125 |
| # of units | | 100 |
| Dewatering per unit | | |
| belt width | ft | 9 |
| algae thickness | ft | 0.0033 |
| speed | ft/min | 2.4 |
| Hp requirement | Hp | 4.7 |
| VS. Using pumps | gpm | 21817 |
| Hp requirement | Hp | 283 |

I claim:

1. A system for harvesting algae in continuous fermentation, said system comprising:
    a harvesting means being comprised of a main moving belt, a plurality of rollers, and a motor means for driving said main moving belt;
    a reactor tank, said main moving belt having one end within an interior of said reactor tank and having at least one roller placed along a predetermined length of said reactor tank;
    a vacuum extraction means for applying a vacuum over a width of said main moving belt to extract a biomass and to dry said main moving belt, said main moving belt having another end extended into said vacuum extraction means;
    a stabilizing means being comprised of at least two belts, said main moving belt being placed between said at least two belts in said vacuum extraction means; and
    a collection means for holding extracted biomass.

2. The system for harvesting algae, according to claim 1, wherein at least one roller of said harvesting means is positioned at a bottom of said reactor tank so as to submerge a portion of said main moving belt for exposure to algae in said reactor tank.

3. The system for harvesting algae, according to claim 1, wherein at least two rollers of said harvesting means are positioned on a bottom of said reactor tank at opposite ends of said reactor tank so as to expose said main moving belt to algae.

4. The system for harvesting algae, according to claim 1, wherein said main moving belt has at least one end extending out of said reactor tank.

5. The system for harvesting algae, according to claim 4, wherein said main moving belt has an inclined surface from said one end within said interior of said reactor tank upward to said one end extending out of said reactor tank.

6. The system for harvesting algae, according to claim 1, wherein said vacuum extraction means is positioned higher than said reactor tank.

7. The system for harvesting algae, according to claim 1, wherein said collection means is at an opposite end of said main moving belt from said reactor tank.

8. The system for harvesting algae, according to claim 1, further comprising:
    a post-extraction means for air drying or washing or both, said post-extraction means being another vacuum over a width of said main moving belt after said main moving belt passes through said vacuum extraction means and said collection means and before returning to said reactor tank.

9. The system for harvesting algae, according to claim 8, wherein said main moving belt has an inclined surface from said vacuum extraction means to said post-extraction means.

\* \* \* \* \*